(12) United States Patent
Do

(10) Patent No.: US 12,075,972 B2
(45) Date of Patent: Sep. 3, 2024

(54) METHOD FOR MANUFACTURING AN INSERTION TUBE OF AN ENDOSCOPE AND ENDOSCOPE COMPRISING AN INSERTION TUBE

(71) Applicant: HOYA CORPORATION, Tokyo (JP)

(72) Inventor: Anh Minh Do, Friedberg (DE)

(73) Assignee: HOYA CORPORATION, Tokyo (JP)

( * ) Notice: Subject to any disclaimer, the term of this patent is extended or adjusted under 35 U.S.C. 154(b) by 645 days.

(21) Appl. No.: 17/281,429

(22) PCT Filed: Oct. 25, 2019

(86) PCT No.: PCT/IB2019/001086
§ 371 (c)(1),
(2) Date: Mar. 30, 2021

(87) PCT Pub. No.: WO2020/089684
PCT Pub. Date: May 7, 2020

(65) Prior Publication Data
US 2021/0393111 A1    Dec. 23, 2021

(30) Foreign Application Priority Data
Oct. 31, 2018    (DE) .................. 10 2018 127 227.8

(51) Int. Cl.
*A61B 1/00* (2006.01)
*A61B 1/005* (2006.01)

(52) U.S. Cl.
CPC ........ *A61B 1/0011* (2013.01); *A61B 1/00098* (2013.01); *A61B 1/0055* (2013.01)

(58) Field of Classification Search
CPC .......................... A61B 1/0011; A61B 1/0055
See application file for complete search history.

(56) References Cited

U.S. PATENT DOCUMENTS 5,329,923 A * 7/1994 Lundquist ......... A61M 25/0147
607/122
6,749,560 B1    6/2004 Konstorum et al.
(Continued)

FOREIGN PATENT DOCUMENTS

| CN | 101632603 A | 1/2010 |
|---|---|---|
| CN | 107666873 A | 2/2012 |

(Continued)

OTHER PUBLICATIONS

Office Action issued in Chinese family member Patent Appl. No. 201980072875.3, dated May 24, 2023.
(Continued)

*Primary Examiner* — Matthew J Kasztejna
(74) *Attorney, Agent, or Firm* — GREENBLUM & BERNSTEIN P.L.C.

(57) ABSTRACT

The invention relates to a method for manufacturing an insertion tube of an endoscope from a tubular element, wherein the insertion tube includes a proximal passive flexible portion and a distal deflecting portion, wherein, in the proximal passive flexible portion, cuts are provided to enable the proximal passive flexible portion to be bent. In the method, the cuts are configured in the proximal passive flexible portion such that adjacent cuts do not have the same distance. The invention further relates to an endoscope including such insertion tube.

20 Claims, 15 Drawing Sheets

(56) References Cited

U.S. PATENT DOCUMENTS

| | | | |
|---|---|---|---|
| 7,708,704 B2* | 5/2010 | Mitelberg | A61M 25/0043 604/528 |
| 7,828,724 B2 | 11/2010 | Hosoi et al. | |
| 7,846,089 B2 | 12/2010 | Maruyama | |
| 8,545,395 B2 | 10/2013 | Akahoshi et al. | |
| 8,845,521 B2 | 9/2014 | Maruyama | |
| 11,627,866 B2* | 4/2023 | Do | A61B 1/0011 604/95.04 |
| 2005/0177132 A1* | 8/2005 | Lentz | A61M 25/0013 604/525 |
| 2005/0272975 A1* | 12/2005 | McWeeney | A61B 1/307 600/172 |
| 2011/0022069 A1 | 1/2011 | Miroslav | |
| 2012/0116163 A1 | 5/2012 | Lutze et al. | |
| 2014/0053940 A1 | 2/2014 | Konstorum et al. | |
| 2014/0163321 A1 | 6/2014 | Seto et al. | |
| 2014/0378767 A1* | 12/2014 | Lee | A61B 1/0055 600/141 |
| 2016/0262754 A1 | 9/2016 | Altman | |
| 2017/0079505 A1 | 3/2017 | Nakade | |
| 2017/0095138 A1 | 4/2017 | Nakade et al. | |
| 2018/0008805 A1 | 1/2018 | Pleijers | |
| 2018/0125339 A1 | 5/2018 | Gerbo et al. | |
| 2020/0237185 A1* | 7/2020 | Do | A61B 1/0011 |
| 2022/0031146 A1 | 2/2022 | Gerbo et al. | |
| 2022/0193371 A1 | 6/2022 | Pleijers | |

FOREIGN PATENT DOCUMENTS

| | | |
|---|---|---|
| CN | 107249426 A | 10/2017 |
| CN | 107530076 A | 1/2018 |
| DE | 100 52 679 A1 | 5/2001 |
| EP | 2 742 879 A2 | 6/2014 |
| EP | 2 777 476 A1 | 9/2014 |
| EP | 3 135 182 A1 | 3/2017 |
| JP | H09-24019 A | 1/1997 |
| JP | 2001-161631 A | 6/2001 |
| JP | 2010-119601 A | 6/2010 |
| JP | 2012-527917 A | 11/2012 |
| WO | 2012/073072 | 6/2012 |
| WO | WO 2012/073072 A1 | 6/2012 |
| WO | WO 2013/190910 A1 | 5/2016 |
| WO | WO 2016/052145 A1 | 4/2017 |
| WO | WO 2017/213491 A1 | 12/2017 |

OTHER PUBLICATIONS

Office Action issued in Japanese family member Patent Appl. No. 2021-523730, dated Sep. 5, 2023, together with an English-language translation.

U.S. Appl. No. 17/284,223 to Anh Minh Do, which was filed Apr. 9, 2021.

U.S. Appl. No. 17/274,300 to Toshiyuki Katayama, which was filed Mar. 8, 2021.

International Search Report issued in International Bureau of WIPO Patent Application No. PCT/IB2019/001086, dated Feb. 17, 2020, along with an English translation thereof.

Written Opinion of the International Searching Authority issued in International Bureau of WIPO Patent Application No. PCT/IB2019/001086, dated Feb. 17, 2020.

Examination Report issued in Australian Counterpart Patent Appl. No. 2019373820, dated Oct. 29, 2021.

International Preliminary Report on Patentability, WIPO, issued in PCT/IB2019/001086, dated Apr. 27, 2021 (with English translation).

Written Opinion of the International Searching Authority, WIPO, issued in PCT/IB2019/001086, dated Feb. 17, 2020 (with English translation).

\* cited by examiner

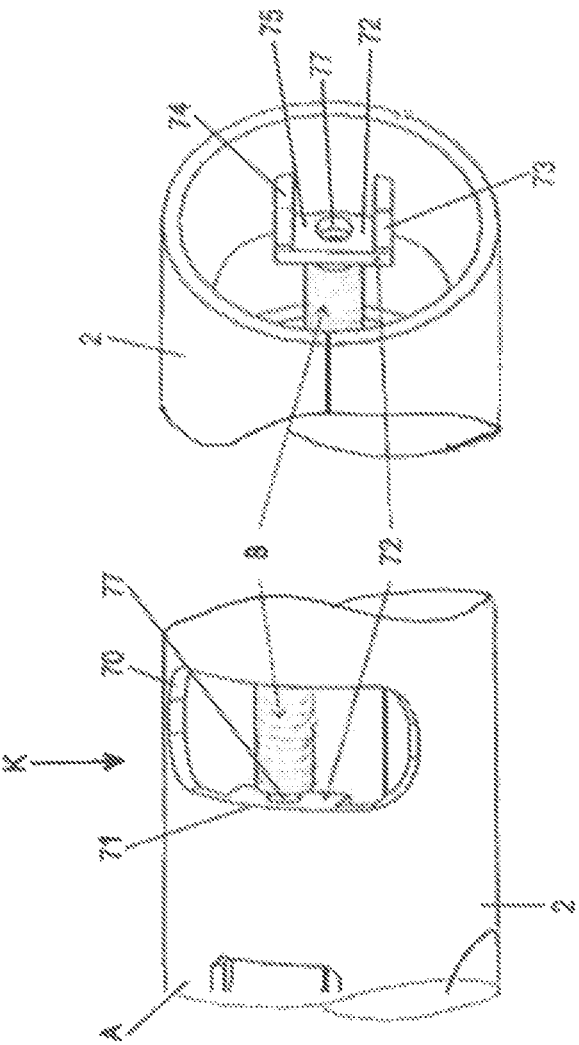

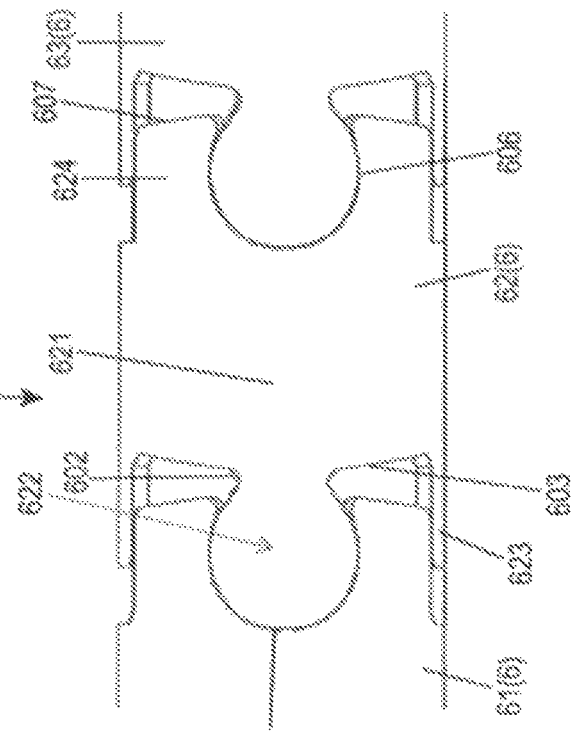

METHOD FOR MANUFACTURING AN INSERTION TUBE OF AN ENDOSCOPE AND ENDOSCOPE COMPRISING AN INSERTION TUBE

The present invention relates to a method for manufacturing an insertion tube of an endoscope and to an endoscope comprising an insertion tube.

An endoscope is a device by which the interior of living organisms but also technical cavities can be examined. An important part of an endoscope is the flexible insertion tube. The requirements made to an insertion tube are high and diverse. On the one hand, it must be flexible so that it can be inserted into the human body. On the other hand, the insertion tube must exhibit specific rigidity. During examination, the physician must be able to push and rotate the insertion tube by means of the control body. Accordingly, the insertion tube must be so rigid that it is not kinked or twisted. Conventional insertion tubes therefore involve a very complex structure and high manufacturing costs to meet the afore-mentioned requirements.

For meeting all requirements, the insertion tube must have various characteristics. Three of the most important characteristics of an insertion tube are flexibility, torsional resistance and dimensional stability. It must be bendable, on the one hand, so that it can be inserted into the (e.g., human) body subject to examination. On the other hand, the insertion tube must have high torsional resistance to transmit the torque generated by the user by way of turning a control body, further to the distal end. Moreover, the insertion tube must not deform when it is bent or rotated.

The requirement that an insertion tube simultaneously must have the afore-mentioned characteristics is a technical contradiction in itself. An element is usually rigid and dimensionally stable when it has a high torsional resistance. When the element has a high flexibility, however, it has no high torsional resistance and is not dimensionally stable.

In order to satisfy the afore-mentioned requirement, developers have attempted for quite some time to design the base area of the insertion tube with plural components. FIG. 25 reveals a known way of structuring a base area of the insertion tube.

In the known solution of FIG. 25, three different components are joined to obtain the relevant characteristics of the base area of an insertion tube 1000, viz. high flexibility, high torsional resistance and high dimensional stability.

A plastic coating 1004 is heated until the material of the inner face partially melts and penetrates gaps of a metal mesh 1003. This combination imparts high torsional resistance and high flexibility to the base area of an insertion tube 1000. However, the dimensional stability is still missing. Accordingly, two metal leaf spirals 1001 and 1002 arranged in opposite directions are used. Said metal leaf spirals 1001 and 1002 ensure the insertion tube to become dimensionally stable. Now the described combination imparts the three stated necessary characteristics to the insertion tube 1000: namely high flexibility, high torsional resistance and high dimensional stability.

A drawback of this complex structure resides in the economic aspect. Three components are joined in an expensive manufacturing process. Both the materials and the manufacturing process incur high manufacturing costs.

It is the object of the present invention to provide a method for manufacturing an insertion tube of an endoscope as well as an endoscope comprising an insertion tube which are less complex and help reduce the costs.

As regards the method, the object is achieved by a method comprising the features of claim 1. An endoscope comprising an insertion tube is illustrated in claim 11. Advantageous developments are the subject matter of the dependent claims.

The invention is directed to a method for manufacturing an insertion tube of an endoscope from a tubular element. The insertion tube has a proximal passive flexible portion and a distal deflecting portion. In the proximal passive flexible portion cuts are provided to enable the proximal passive flexible portion to be bent. These cuts are configured in the proximal passive flexible portion such that adjacent cuts do not have the same distance from each other.

In the insertion tube according to the invention, cuts are produced that do not have the same distance. The distances between cuts produced in the insertion tube thus are different from each other. The cuts may be produced perpendicularly to the axis of the insertion tube.

In one example, when viewed in the longitudinal direction of the insertion tube, plural adjacent cuts can be produced so that a distance between first and second adjacent cuts is a predetermined distance and a distance between the second and third adjacent cuts is smaller or larger than the predetermined distance.

In another example, when viewed in the longitudinal direction of the insertion tube, plural adjacent cuts can be produced so that a distance between first and second adjacent cuts is a predetermined distance, and a distance between the second cut and a third adjacent cut is equal to the predetermined distance, but a distance between the third cut and a fourth adjacent cut is smaller or larger than the predetermined distance.

The different distances of the cuts result, in the longitudinal direction of the insertion tube, in regions having a large distance between the cuts and in regions having a small distance between the cuts. The region having a large distance between the cuts ensures high bending stability and high resistance to torsion. The region having a small distance between the cuts ensures high bendability and high flexibility. The exact dimensions for the distances can be selected as needed.

In the proximal passive flexible portion, main cuts may be provided which have the same distance from each other in the longitudinal direction of the proximal passive flexible portion, and, adjacent to the main cuts, secondary cuts may be provided in the proximal passive flexible portion which are arranged, in the longitudinal direction of the proximal passive flexible portion, to be closer to the adjacent main cuts on one side of the secondary cuts than to the adjacent main cuts on the other side of the secondary cuts.

The main cuts can be cut in parallel to each other.

The main cuts can be cut in an interrupted manner along the periphery of the proximal passive flexible portion so that non-cut stays are left between main cut portions located on a peripheral line.

The secondary cuts can be cut adjacent to a respective stay between main cut portions located on a peripheral line.

One secondary cut can be respectively cut in the longitudinal direction of the proximal passive flexible portion adjacent to the stay on one side of the stay.

Alternatively, two secondary cuts can be respectively cut in the longitudinal direction of the proximal passive flexible portion adjacent to the stay on both sides of the stay.

The main cuts can be cut to be wider than the secondary cuts.

The whole insertion tube can be manufactured including a connecting region of the proximal passive flexible portion at a control body, the proximal passive flexible portion, a transition region between the proximal passive flexible portion and the deflecting portion, and the deflecting portion from one single tubular element.

The whole insertion tube can be cut by laser.

In one example of the method, only one tubular element must be provided. A connecting operation between the proximal passive flexible portion and the distal deflecting portion is omitted. The production costs are lower than in previous methods for manufacturing an insertion tube.

In this method, the whole insertion tube including the deflecting portion can be cut by laser from one single tubular element. The laser machining allows for a high-precision design of the whole insertion tube.

In this method, individual cuts can be made in the tubular element. This renders manufacture easy and inexpensive.

In this method, the distal deflecting portion has inwardly bent guiding projections on which a pull cable is supported; wherein the inwardly bent guiding projections are cut out of the peripheral wall of the distal deflecting portion and then are bent inward. Thus, guides for a pull cable are produced in a simple manner on the inner peripheral side of the deflecting portion.

In this method, the insertion tube includes, at the transition from the proximal passive flexible portion and the distal deflecting portion, an inwardly bent tab on which a guide spring is supported; the inwardly bent tab being cut out of the peripheral wall of the insertion tube and then being bent inward. The number of the inwardly bent tabs on which a guide spring is supported corresponds to the number of guide springs and thus the number of pull cables. In this way, guides for guide springs are produced in a simple manner on the inner peripheral side of the insertion tube.

In this method, in the peripheral wall of the distal deflecting portion plural joints can be produced by cutting. Individual joints forming separate bodies and being positively connected to each other are produced in a simple and inexpensive manner.

In this method, the respective joint produced by cutting includes a coupling portion which is coupled to an adjacent joint produced by cutting such that an axial movement but no radial movement of the joints relative to each other is blocked, and a guiding portion engaged in an adjacent joint produced by cutting in such a manner that an axial movement of the joints relative to each other is possible. The coupling portion helps couple adjacent joints to each other and the guiding portion renders adjacent joints axially movable relative to each other.

In this method, the proximal passive flexible portion is produced by respective lateral incisions made perpendicularly to the longitudinal extension of the tubular element. Thus, the proximal passive flexible portion can be quickly and simply manufactured.

In this method, in the longitudinal extension of the tubular element, the proximal passive flexible portion has at least two sub-portions including the respective lateral incisions (cuts) at a distance different from each other in the longitudinal extension of the tubular element. Thus, plural separate sub-portions having different flexibility and bendability relative to each other can be formed in the proximal passive flexible portion.

In this method, the tubular element may be produced from stainless steel. The cuts can be easily produced. The material costs are low.

In this method, the tubular element can be produced from plastic material. Any suitable plastic material having sufficient strength may be employed. The plastic material merely must be capable of producing the bendability of the finished insertion tube.

In this method, a pull cable can be arranged from a control body disposed proximally from the proximal passive flexible portion on the inner peripheral side of the tubular element, which pull cable is guided on a most distally located joint of the distal deflecting portion through a first slit in a wall of the tubular element to the outer periphery of the tubular element, is guided around the outer periphery of the tubular element to a second slit in the wall of the tubular element to the inner periphery of the tubular element, with the second slit being opposed to the first slit by 180 degrees, and is returned to the control body on the inner peripheral side of the tubular element. In this way, an especially inexpensive anchoring of the pull cable on the distal side of the deflecting portion can be effectuated.

The endoscope according to the invention includes an insertion tube. The insertion tube includes a proximal passive flexible portion and a distal deflecting portion. In the proximal passive flexible portion cuts are provided to allow for bending of the proximal passive flexible portion. Adjacent cuts do not have the same distance in the proximal passive flexible portion.

In this endoscope, the proximal passive flexible portion can include main cuts which have the same distance from each other in the longitudinal direction of the proximal passive flexible portion, and the proximal passive flexible portion can include, adjacent to the main cuts, secondary cuts which are arranged, in the longitudinal direction of the proximal passive flexible portion, to be closer to the adjacent main cuts on one side of the secondary cuts than to the adjacent main cuts on the other side of the secondary cuts.

In this endoscope, the main cuts may be parallel to each other.

In this endoscope, the main cuts may extend along the periphery of the proximal passive flexible portion in an interrupted manner such that non-cut stays are left between main cut portions located on a peripheral line.

In this endoscope, the secondary cuts may be arranged adjacent to a respective stay between main cut portions located on a peripheral line.

In this endoscope, a secondary cut may be respectively arranged in the longitudinal direction of the proximal passive flexible portion adjacent to the stay on one side of the stay.

In this endoscope, alternatively two secondary cuts may be arranged in the longitudinal direction of the proximal passive flexible portion respectively adjacent to the stay on both sides of the stay.

In this endoscope, the main cuts may be wider than the secondary cuts.

In this endoscope, the whole insertion tube including a connecting region of the proximal passive flexible portion at a control body, the proximal passive flexible portion, a transition region between the proximal passive flexible portion and the deflecting portion, and the deflecting portion can be manufactured from one single tubular element.

In this endoscope, the whole insertion tube may be cut by laser.

Further, the whole insertion tube including the passive flexible portion and the deflecting portion may be formed of one single tubular element.

The distal deflecting portion may have inwardly bent guiding projections on which a pull cable is supported.

The insertion tube may include, at the transition from the proximal passive flexible portion and the distal deflecting portion, an inwardly bent tab on which a guide spring is supported.

Plural joints may be formed in the peripheral wall of the distal deflecting portion.

Each joint may include a coupling portion coupled to an adjacent joint such that an axial movement but no radial movement of the joints relative to each other is blocked, and a guiding portion engaged in an adjacent joint such that an axial movement of the joints relative to each other is enabled.

The tubular element may be manufactured from stainless steel or from plastic material.

From a control body disposed proximally from the proximal passive flexible portion a pull cable can be arranged on the inner peripheral side of the tubular element, which pull cable is guided at a most distally located joint of the distal deflecting portion through a first slit in a wall of the tubular element to the outer periphery of the tubular element, is guided around the outer periphery of the tubular element to a second slit in the wall of the tubular element to the inner periphery of the tubular element, with the second slit being opposed to the first slit by 180 degrees, and is returned to the control body on the inner peripheral side of the tubular element.

The afore-described aspects of the present invention can be combined in a suitable manner.

BRIEF DESCRIPTION OF THE DRAWING

FIG. 11 shows a fragmentary schematic view of a transition region between the distal deflecting portion and the proximal passive flexible portion of the insertion tube according to the invention, with a guide spring fixing portion being shown.

FIG. 12 shows a fragmentary perspective view of the guide spring fixing portion from FIG. 11 from another side.

FIG. 13 shows a fragmentary schematic view of part of the deflecting portion of the insertion tube according to the invention.

FIG. 14 shows a fragmentary schematic view of the part of the deflecting portion of the insertion tube according to the invention, showing a view from the direction of an arrow I from FIG. 13.

Figure 19:
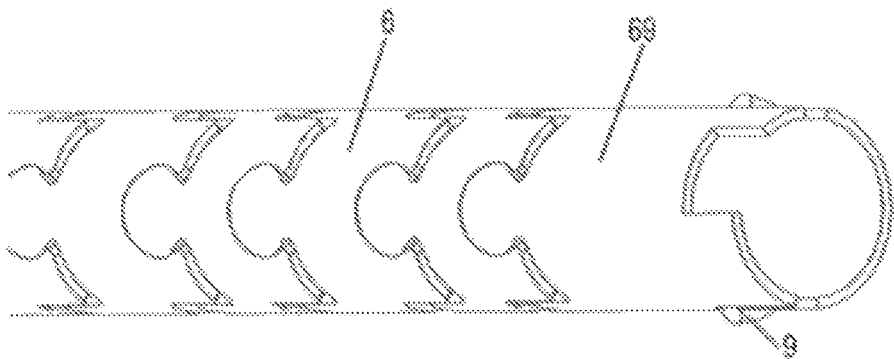
Figure 20:
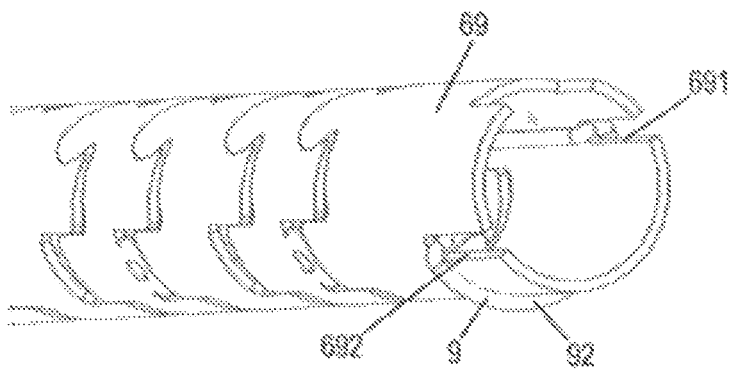
Figure 21:
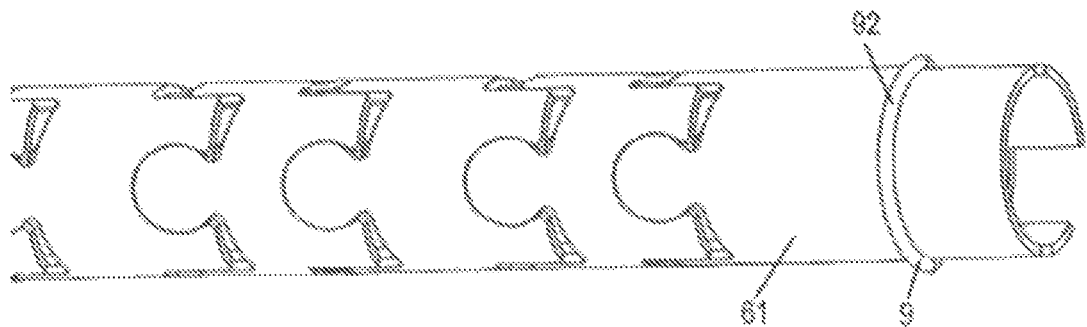

Each of FIGS. 19 to 21 shows a fragmentary perspective view of the distal end of the deflecting portion.

Figure 22:
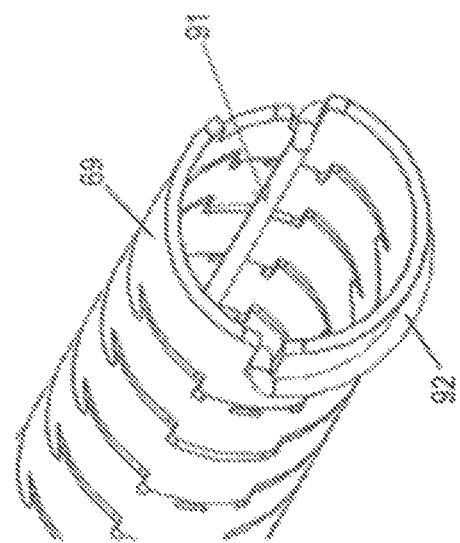

FIG. 22 shows a fragmentary perspective view of the pull cable anchoring at the distal end of the deflecting portion.

Figure 23:
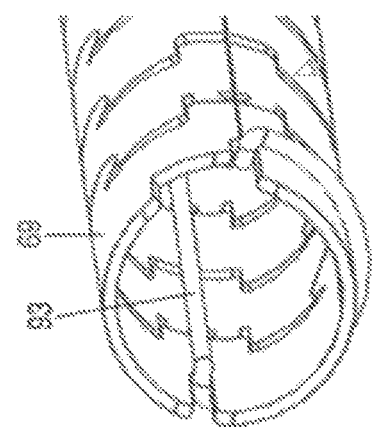

FIG. 23 shows a view corresponding to FIG. 22 from another side.

Figure 24:
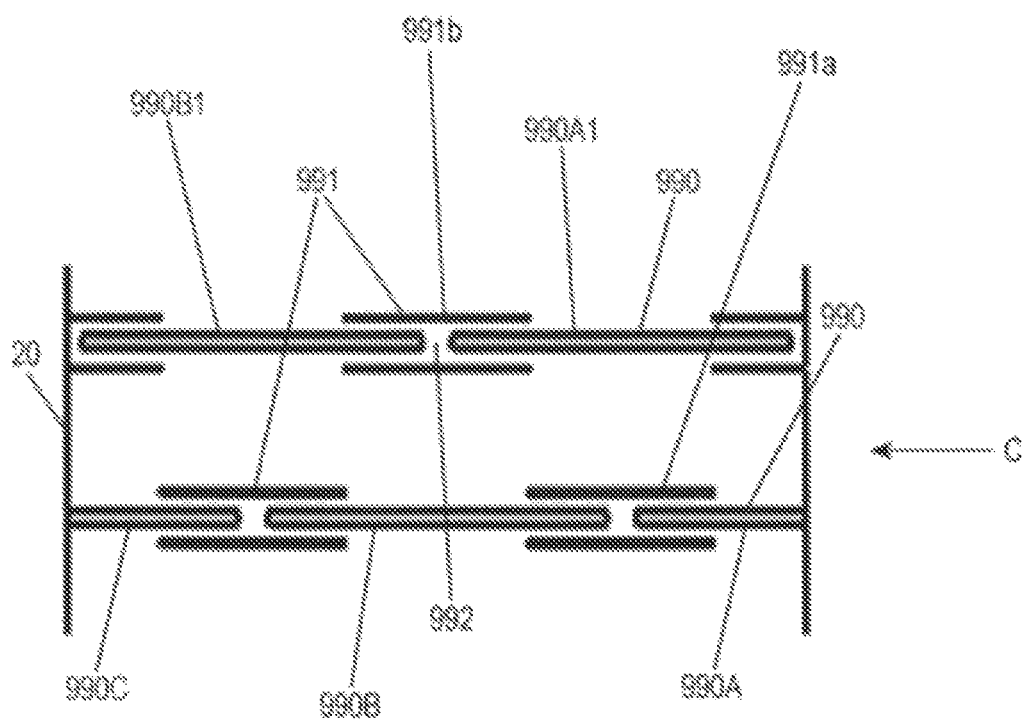

FIG. 24 shows a fragmentary schematic representation of the proximal passive flexible portion in a second embodiment.

Figure 25:
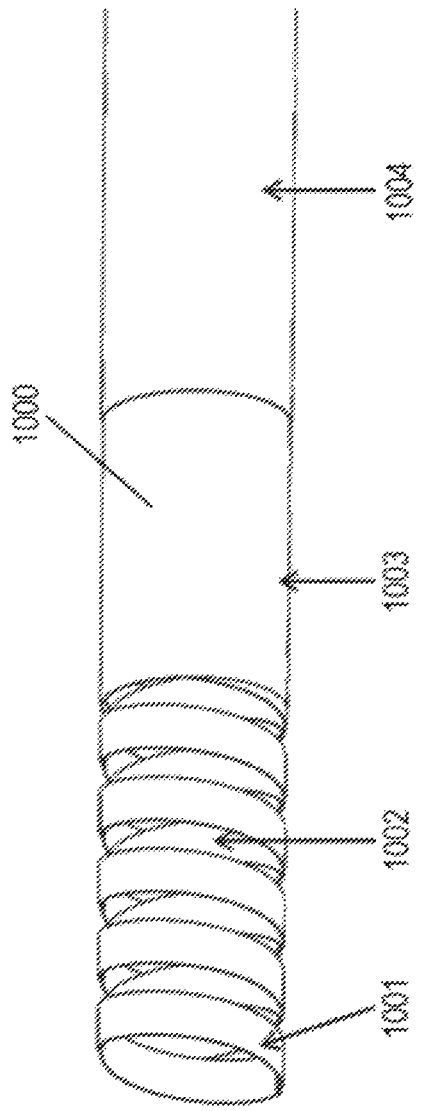

FIG. 25 shows a fragmentary perspective view of a state-of-the-art insertion tube.

Hereinafter, the present invention shall be described in detail with reference to the drawings by way of embodiments.

FIRST EMBODIMENT

Hereinafter, with reference to FIGS. 1 to 23, a first embodiment of the present invention shall be described.

Figure 1:
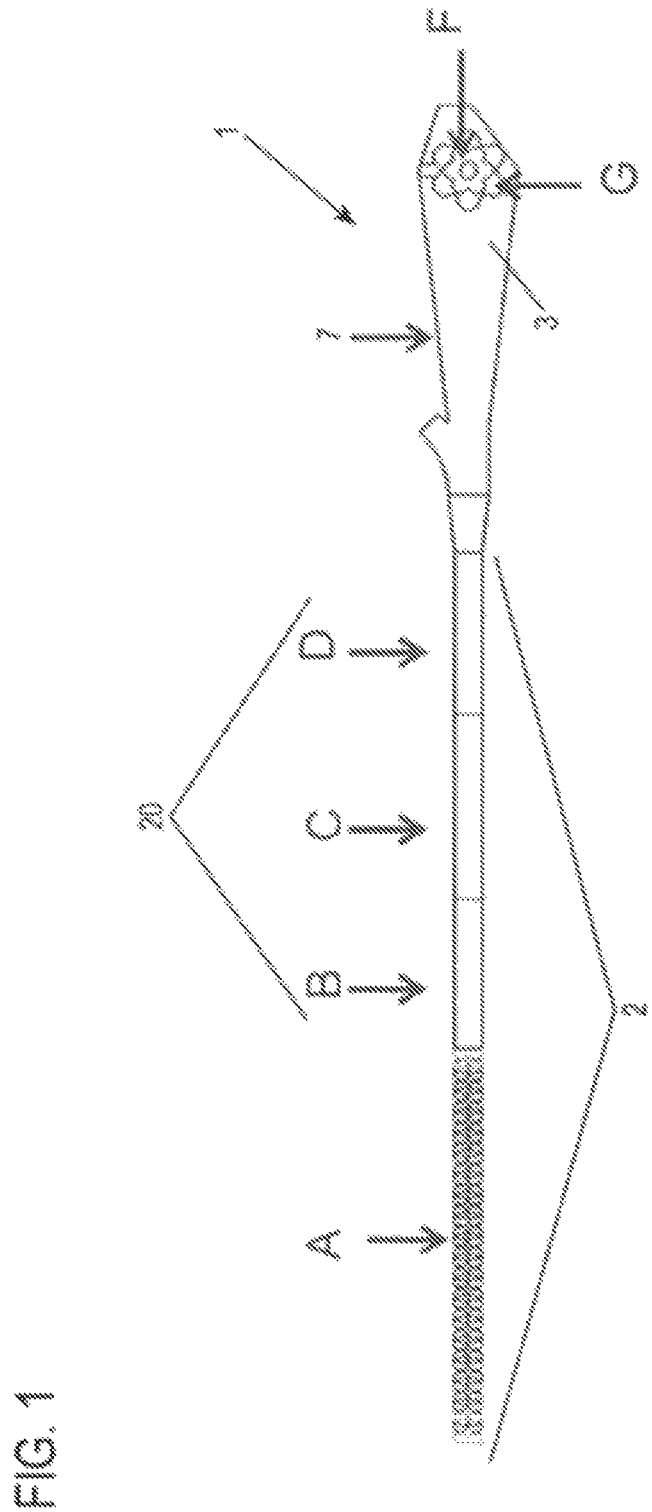
FIG. 1 shows a schematic side view of an endoscope to which the invention can be applied.

First of all, FIG. 1 shows a schematic side view of an endoscope 1 to which the invention is applicable. As can be inferred from FIG. 1, such endoscope 1 includes an insertion tube 2 disposed on the distal side of a control body 3. The control body 3 serves as operating unit of the endoscope 1.

The insertion tube 2 is a cylindrical tube-shaped or hose-shaped structure.

Hereinafter, the insertion tube 2 is described in more detail in the direction in which it is inserted into a patient. The insertion tube 2 is inserted with the distal end ahead.

On the distal side, the insertion tube 2 has a distal deflecting portion A. The deflecting portion A can be laterally deflected by means of one or more control wires (control cable(s)) relative to the proximal part of the insertion tube 2. The control wire or control cable (hereinafter only referred to as control wire) is supported inside the insertion tube 2 on an inner peripheral surface of the insertion tube 2 to be guided in the direction of extension of the insertion tube 2.

The distal end of the control wire is anchored on the distal side of the deflecting portion A. The proximal end of the control wire is connected to a control element disposed in the control body 3. Said control element tensions the control wire to bring about a desired deflection of the deflecting portion A.

Proximally from the deflecting portion A, the insertion tube 2 is designed as a flexible hose member forming a proximal passive flexible portion 20. During insertion of the insertion tube 2, the flexible portion 20 follows the deflecting portion A.

It is indicated in FIG. 1 that the flexible portion 20 is designed along its longitudinal direction in zones having different flexibility. For example, the flexible portion 20 has a first zone B, a second zone C and a third zone D, when viewed in the proximal direction. The first zone B forms a distal region, the second zone C forms a central region and the third zone D forms a proximal region.

Figure 2:
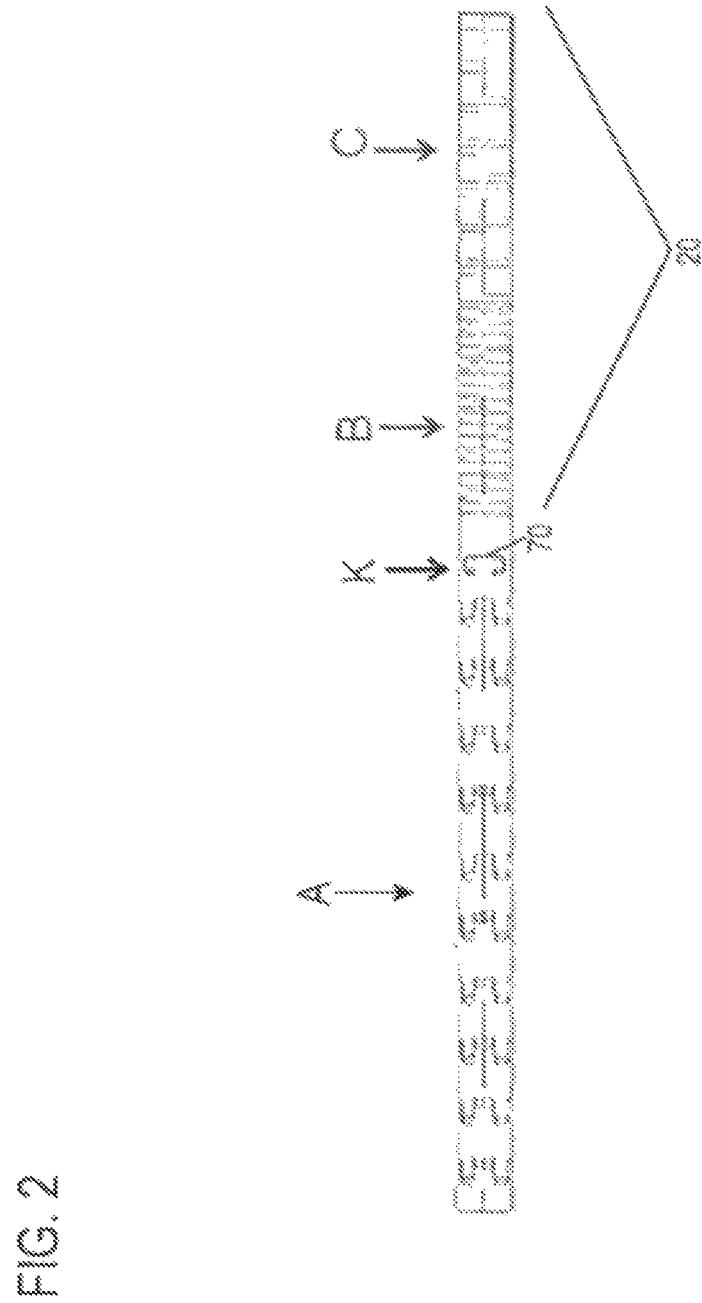
FIG. 2 shows a fragmentary schematic view of an insertion tube according to the invention.

In the fragmentary representation of FIG. 2, the third zone D is not shown.

For avoiding kinking between the deflecting portion A and the first zone B, the first zone B is preferably provided with the maximum flexibility among the zones of the flexible portion 20. Since the first zone B is equipped with very high flexibility, there is no abrupt transition of flexibility between the deflecting portion A and the first zone B.

The second zone C has lower flexibility than the first zone B. The third zone D in turn has lower flexibility than the second zone C.

The insertion tube 2 according to the invention is formed of one piece. That is, there are not joined two elements at the transition from the deflecting portion A to the flexible portion 20. Thus, the distal deflecting portion A and the proximal passive flexible portion 20 are formed with the three zones B, C and D of one single tube or hose.

On the proximal side, the insertion tube 2 is fixed at the distal end of the control body 3. The insertion tube 2 can be fixed to the control body 3, e.g., by a locking ring, a seal ring or directly. The insertion tube 2 may be glued or screwed, for example, to the control body 3. The control body 3 includes a first control wheel F as first control element for controlling a control wire or cable and a second control wheel G as second control element for controlling a control wire or cable. The first control wheel F can deflect the deflecting portion A in a first plane by pulling a control wire or cable (e.g., toward the viewer and away from the viewer in FIG. 1). The second control wheel G can deflect the deflecting portion A in a second plane perpendicular to the first plane by pulling a control wire or cable (e.g., upward and downward in FIG. 1).

The deflecting portion A can be deflected, e.g., about 200-270 degrees. This is sufficient for most applications. In a special form, the deflecting portion A can be deflected even about 300 degrees.

In the following, the insertion tube 2 according to the invention and the manufacture thereof are described in greater detail.

The whole insertion tube 2 is formed of one single tubular element or hose member (hereinafter this is simply referred to as tubular element). The tubular element is a tube made from preferably relatively hard material. A tube made from stainless steel is especially preferred. However, also a tube made from hard plastic can be applied. On principle, any material applicable for medical purposes can be used.

In the tubular element cuts are provided by a laser cutting machine, as illustrated in detail further below. After providing the cuts, particular segments of the tubular element are bent as illustrated in detail further below. The manufacture of the base body of the whole insertion tube 2 requires no further process steps apart from providing cuts and bending. After that, the base body of the insertion tube 2 can be provided with a control wire and can be encased by a jacket element.

Hereinafter, the individual portions of the insertion tube 2 shall be described in detail.

Flexible portion 20

The flexible portion 20 forms the proximal part of the insertion tube 2 according to the invention. The flexible portion 20 includes the three zones B, C and D each having different flexibility.

For clarity, FIG. 1 shows the proximal passive flexible portion 20 as if the three zones B, C and D were equal in length to each other along the longitudinal direction of the insertion tube 2, which, of course, is not the case. The central zone C is longer than the transition region B and the connecting region D. Among the three zones B, C and D, the central zone C in the proximal passive flexible portion 20 is the longest one. In other words, the actual proximal passive flexible portion 20 is formed by the structure of the central region C. The bending characteristics, the elasticity and the torsional resistance of the proximal passive flexible portion 20 are materialized by the structure of the central region C.

Hereinafter, the structure of the central region C and thus of the actual proximal passive flexible portion 20 shall be described in detail by way of FIGS. 3 to 10.

Figure 3:
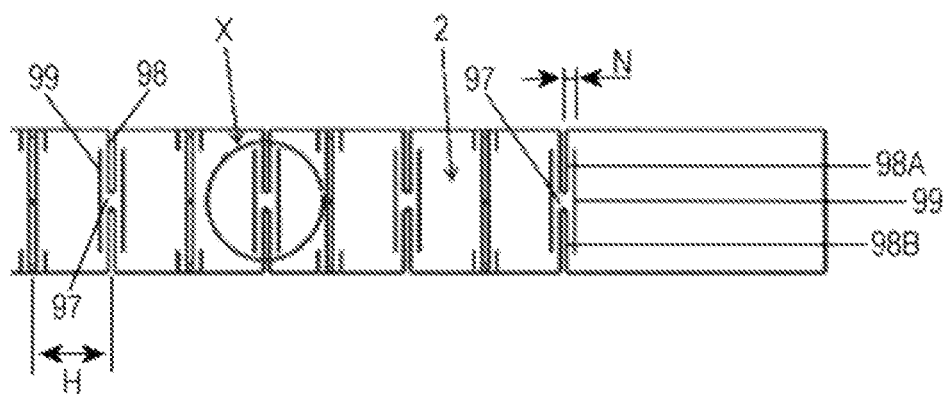
FIG. 3 shows a fragmentary schematic side view of part of a proximal passive flexible portion of the insertion tube according to the invention of a first embodiment.

FIG. 3 illustrates a fragmentary schematic side view of part of a proximal passive flexible portion of the insertion tube according to the invention of a first embodiment.

Figure 4:
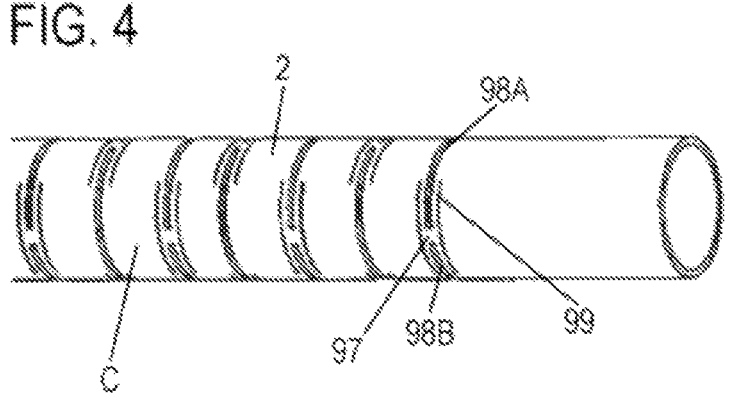
FIG. 4 shows a fragmentary perspective view of the part of the proximal passive flexible portion from FIG. 3.
Figure 5:
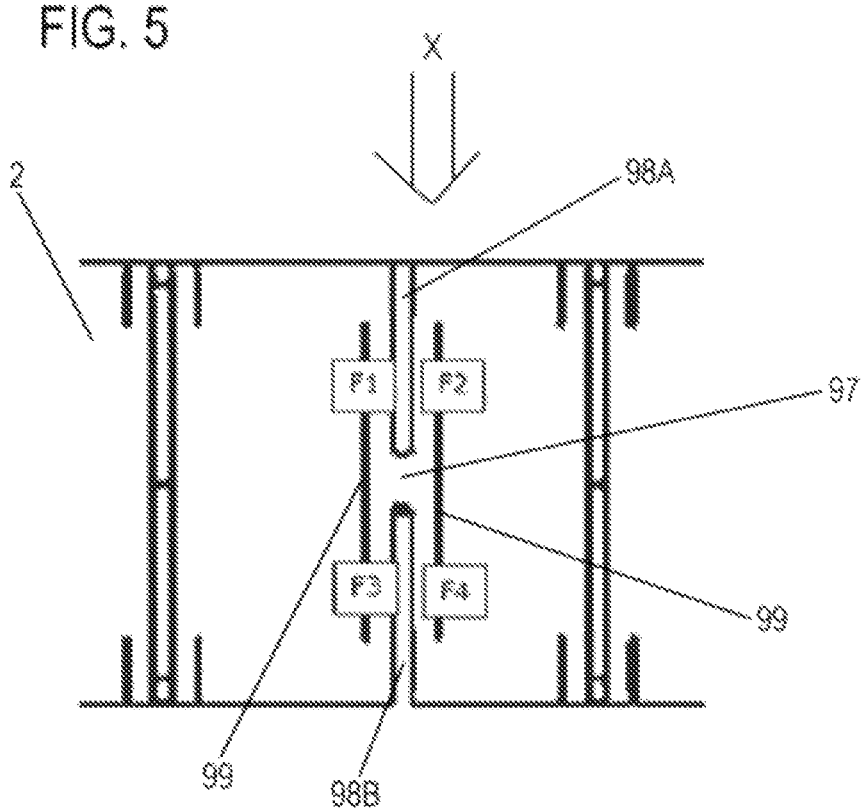
FIG. 5 shows a detail of the proximal passive flexible portion of FIG. 3 for illustrating the bending resistance.

FIG. 4 illustrates a fragmentary perspective view of the part of proximal passive flexible portion of FIG. 3.

The cut design according to the invention of the first embodiment is evident from FIGS. 3 and 4.

When manufacturing said cut design, a tube 2 is used as raw material. The tube 2 has an axis and a longitudinal extension. The tube 2 consists of a sufficiently hard material. For example, stainless steel can be used. Plastic material or a nickel-titanium alloy such as Nitinol can equally be used. The tube 2 later constitutes the insertion tube according to the invention.

The tube 2 takes a shape which initially is not flexible. The tube 2 has high torsional resistance and high dimensional stability.

In this tube 2, at predetermined distances H main cuts 98 are produced preferably by laser at the periphery in the peripheral direction. By peripheral direction a direction is meant which extends at right angles with the axis of the tube 2. Along the tube 2, the respective distance H is equal.

The main cuts 98 penetrate the thickness of the jacket of the tube 2. The main cuts 98 extend in the peripheral direction of the tube 2 over approximately half a peripheral length. Thus, for each peripheral line two main cut portions 98A, 98B successive in the peripheral direction are produced. A stay 97 at which the material of the tube 2 is not cut is provided between the respective main cut portions 98A, 98B. When viewed in the longitudinal direction of the tube 2, the region ahead of and behind (proximal and distal of) the respective main cut 98 is connected via the stay 97. Thus, at each peripheral line for the main cut 98 there are provided two stays 97. The two stays 97 are arranged to be diametrically opposed at each peripheral line for the main cut 98. When viewed in the peripheral direction, a length of a main cut portion 98A, 98B plus a length of the stay 97 exactly is 180°. The length of the main cut portion 98A and the length of the main cut portion 98B are equal to each other.

The stays are offset with respect to each other about 90° from the main cut 98 to the next main cut 98 along the longitudinal direction of the tube 2, as is evident from FIGS. 3 and 4.

In the longitudinal direction of the tube 2, secondary cuts 99 are produced proximally and distally of each stay 97. The secondary cuts 99 extend in parallel to the main cut portions 98A, 98B. The length of the secondary cuts 99 in the peripheral direction is longer than the length of the stay 97 in the peripheral direction. The length of the respective secondary cuts 99 is equal to each other.

In the longitudinal direction of the tube 2, the distance N of each secondary cut 99 from its adjacent main cut portions 98A, 98B is smaller than the distance H of the main cuts 98.

Thus, a proximal secondary cut 99 and a distal secondary cut 99 are associated with each main cut 98 consisting of the two main cut portions 98A, 98B.

Figure 9:
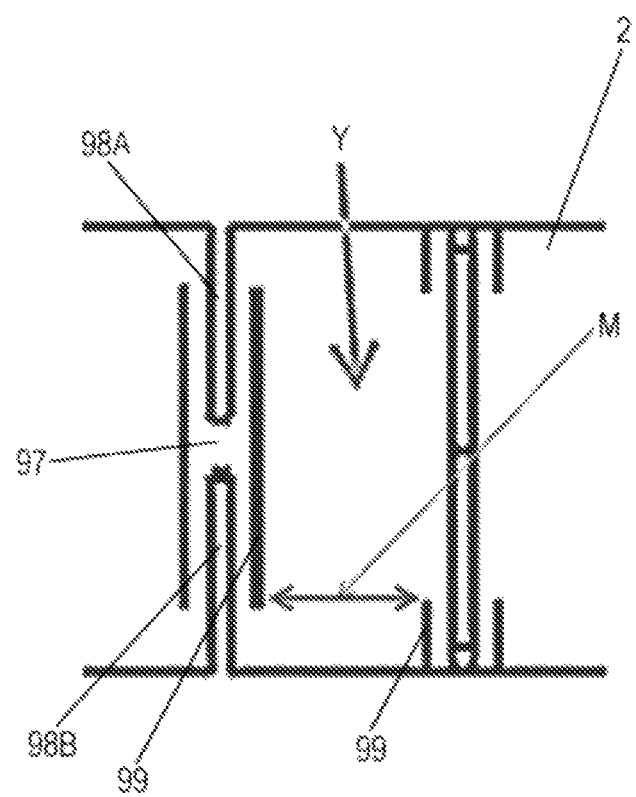
FIG. 9 shows a detail of the proximal passive flexible portion of FIG. 3 for illustration of the torsional resistance.

In the longitudinal direction of the tube 2, the distance N of each secondary cut 99 from its adjacent main cut portions 98A, 98B is equally smaller than the distance M of each secondary cut 99 from its adjacent secondary cut 99 that is associated with the next main cut 98, see FIG. 9.

The characteristic of the tube 2 changes by the main cuts 98 and secondary cuts 99. The tube 2 becomes flexible. The flexibility and other characteristics of the tube 2 are strongly dependent, inter alia, on the design of the cuts 98, 99. More exactly speaking, the cut width, the cut length and the distances of the tube cuts are, inter alia (apart from the material), crucial factors that have an effect on the characteristics of the tube 2.

In the region X, the cut design is provided which is responsible for the creation of the high flexibility of the tube 2.

Hereinafter, the connection between the deformation and the distance between tube cuts during bending will be explained.

In its original shape without any cuts, a tube has a particular bending resistance. As soon as said tube is cut, the bending resistance decreases corresponding to the shape and the number of the cuts provided in the tube. The graphic representation in FIG. 6 illustrates the connection between the deformation and the distance between tube cuts when the tube is bent.

Figure 6:
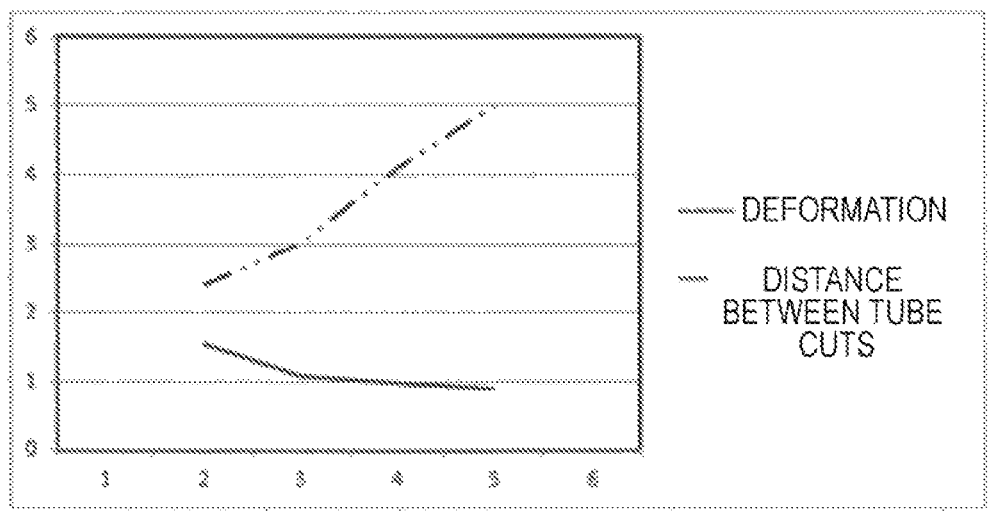
FIG. 6 shows a connection between the deformation and the distance between tube cuts during bending with respect to the bending resistance.

FIG. 6 shows the results of a bending simulation of a tube provided with cuts. The deformation of a tube provided with cuts during a bending operation is shown.

The double dot-and-dash line indicates the distance of a cut from its adjacent cut.

The continuous line indicates the deformation of the tube during bending.

Each of the ordinate and the abscissa show length units (e.g., mm).

The following is visible from FIG. 6: The larger the distance between the tube cuts, the larger the bending resistance becomes (the lower the deformation becomes). If the distance between the tube cuts become infinite, the tube 2 reaches its originally maximum bending resistance.

Since low bending resistance (and thus high flexibility) is required for an insertion tube of an endoscope, consequently a distance between the tube cuts must be as small as possible.

In accordance with the invention, the region X is designed such that the cuts 98 and 99 are close to each other (small distance N) and four spring-type portions F1, F2, F3 and F4 are formed. If the cut tube 2 is bent, the portions F1, F2, F3 and F4 are stretched and a spring-type counter-force is thus resulting. If the tube 2 is relieved after bending, the counter-force acts upon the tube 2 so that the latter recovers its linear shape. Along the longitudinal direction of the tube 2, this design of the region X is repeatedly offset by 90°, namely along the entire length of the proximal passive flexible portion C of the tube 2. In this way, the tube 2 is evenly flexible in all directions.

Figure 7:
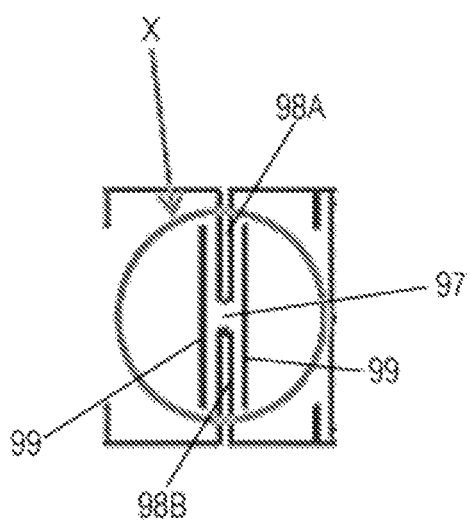
FIG. 7 shows a detail of the proximal passive flexible portion of FIG. 3 for further illustration of the bending resistance.

FIG. 7 shows the region X as an enlarged detail. In the design of a main cut 98 composed of a first main cut portion 98A and a second main cut portion 98B with the associated secondary cuts 99 in the region X, the distance N between the main cut portions 98A, 98B and the associated secondary cuts 99 is intended to be as small as possible to create high flexibility.

Hereinafter, the torsional resistance shall be explained by way of a tube.

Figure 8:
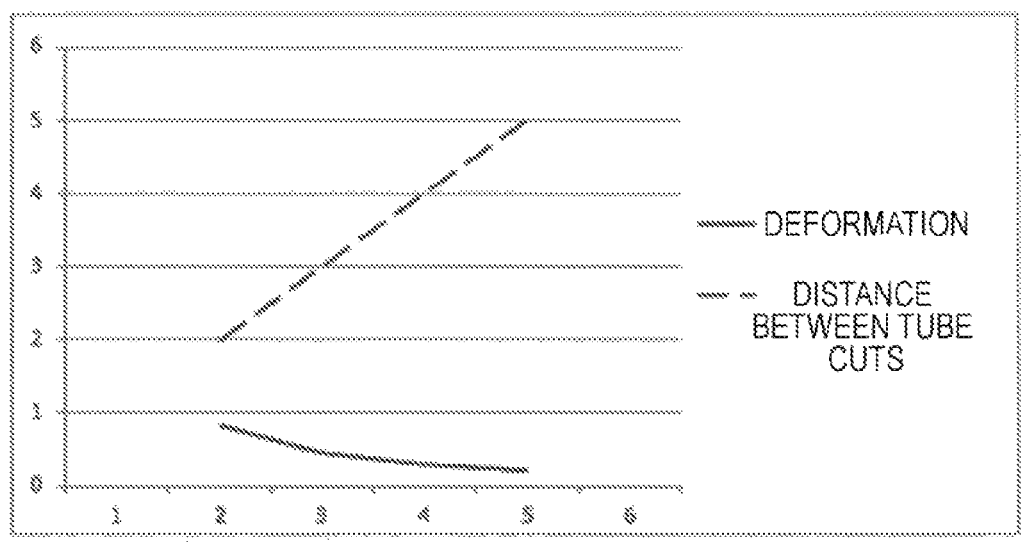
FIG. 8 shows a connection between the deformation and the distance between tube cuts during bending with respect to the torsional resistance.

FIG. 8 illustrates a connection between the deformation and the distance between tube cuts during bending with regard to the torsional resistance. In other words, the graphical representation of FIG. 8 illustrates the connection between the deformation and the distance between tube cuts if the tube is twisted.

FIG. 8 shows the results of a twist simulation of a tube provided with cuts. The deformation of a tube provided with cuts during a twisting operation is shown.

The broken line indicates the distance of a cut from its adjacent cut.

The continuous line indicates the deformation of the tube during twisting.

Each of the ordinate and the abscissa indicates length units (e.g., mm).

The following is evident from FIG. 8: A tube in its original shape without cuts has a particular torsional resistance. As soon as said tube is cut, the torsional resistance decreases corresponding to the shape and the number of the cuts. The larger the distance between the tube cuts, the larger the torsional resistance becomes (and the smaller the deformation becomes during rotation). If the distance between tube cuts becomes infinite, the tube reaches its originally maximum torsional resistance.

Since high torsional resistance is required for an insertion tube of an endoscope, the distance between tube cuts consequently is intended to be as large as possible.

FIG. 9 illustrates in a region Y in an enlarged detail the distance M of each secondary cut 99 from its adjacent secondary cut 99 which is associated with the next main cut 98.

The design in the area Y shows that the distance M between adjacent secondary cuts 99 is intended to be as large as possible to create high torsional resistance. The exact distance M between adjacent secondary cuts 99 can be determined as individually required.

Hereinafter, achieving the dimensional stability on the tube 2 shall be explained.

A hard tube is naturally dimensionally stable. The region Y is designed so that the tube 2 maintains the dimensional stability after it has been provided with a plurality of cuts 98, 99.

The secondary cuts 99 are arranged at such a large distance here that the region Y is relatively long in the longitudinal direction of the tube 2. In other words, a wide annular region that is free from cuts forms in the region Y.

The region Y can be regarded as a short tube and therefore has high dimensional stability. If the entire tube 2 is bent, the portions F1, F2, F3 and F4 will yield (will give way), because the region Y has an inherent stability.

The tube 2 thus is flexible and at the same time dimensionally stable.

Hereinafter, the interaction of the regions X and Y shall be explained.

The entire design of the proximal passive flexible portion C is a combination between the regions X and Y.

Each of said regions X and Y imparts a particular characteristic to the tube 2.

In the region X, the main cuts 98 and the secondary cuts 99 are arranged closely to each other to achieve high flexibility.

In the region Y, however, the secondary cuts 99 have a larger distance from each other to achieve high torsional resistance.

This results in the following interactions between the region X and the region Y:

In the region Y, the secondary cuts 99 have a large distance from each other. This region Y thus is stable both during bending and during twisting. During bending, the region Y remains almost unchanged. The region X, on the other hand, yields and defines the flexibility of the entire tube 2. The effect of the region Y on the flexibility of the tube 2 is insignificant.

In the region X, the main cuts 98 and secondary cuts 99 are arranged very closely to each other.

In the embodiment, the main cuts 98 and the secondary cuts 99 have a cutting width different from each other. By cutting width the width of the respective cut in the longitudinal direction of the tube is meant. If the main cuts 98 and the secondary cuts 99 are produced by laser, the cutting width is adjusted by selecting the diameter of the emitted laser beam.

The cutting width of the secondary cuts 99 is intended to be kept as small as possible. By means of a laser a cutting width, e.g., of far less than 20 µm can be provided. For example, the secondary cuts 99 can be produced to have a cutting width of 20 µm. The main cuts 98 can be produced to have a cutting width of 0.2 mm, for example. These values of the cutting width are merely examples. The appropriate cutting widths can be established by tests. Preferably, the cutting width of the main cuts 98 is larger than the cutting width of the secondary cuts 99. For example, the cutting width of the main cuts 98 may be ten times the cutting width of the secondary cuts 99. This value, too, is merely an example. The appropriate factor may be adjusted as required. The invention is not limited to these values.

Figure 10:
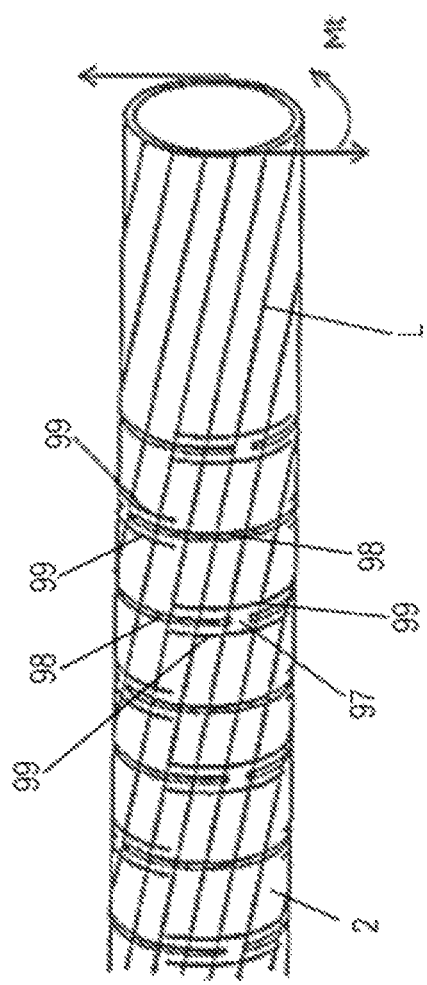
FIG. 10 shows a fragmentary perspective view of part of the proximal passive flexible portion of the first embodiment of FIG. 3 under torsional stress.

Under torsional stress the tube 2 is loaded with a torsional moment Mt acting around the longitudinal axis of the tube 2. By the impact of the torsional moment, imaginary longitudinal lines L of the tube 2 extending in parallel to the longitudinal axis will deform helically, as shown in FIG. 10. Since the distance N of the main cuts 98 and secondary cuts 99 is very small in the region X, the deformation of the region X will differ only slightly from that of the region Y. The torsional resistance of the region Y defines the torsional resistance of the entire tube 2. The impact of the region X on the torsional resistance of the tube 2 is insignificant.

By producing cuts having distances different from each other as afore-described, in the proximal passive flexible portion C of the tube 2 both high flexibility and high torsional resistance can be achieved.

Thus, the endoscope tube 2 according to the invention is bendable in the proximal passive flexible portion C of the flexible portion 20 with high flexibility as well as with high torsional resistance laterally to the longitudinal axis thereof.

The individual zones B, C and D in the flexible portion 20 differ by the distances H of the cuts 98 in the longitudinal direction and thus the density of the cuts 98 being differently configured.

In the zone B, the distance H of the cuts 98 is minimum. Thus, in the zone B the density of the cuts 98 is maximum.

In the zone C, the distance H of the cuts 98 is larger than in the zone B. In the zone D the distance H of the cuts 98 is larger than in the zone C.

Consequently, the flexibility and the bendability are higher in the zone B than in the zone C. Furthermore, the flexibility and the bendability are higher in the zone C than in the zone D. In other words, the flexibility and the bendability of the respective zones decrease at the flexible portion 20 in the proximal direction.

The zone D is provided, on the proximal side, with a region that is not provided with cuts. This region forms a transition to the control body 3.

Transition from the deflecting portion A to the flexible portion 20

The transition region from the deflecting portion A to the flexible portion 20 is indicated as region K in FIG. 2. The deflecting portion A ends in said region K. In other words, the most proximally located first member of the deflecting portion A is located distally from the region K.

As shown in FIGS. 2, 11 and 12, in said region K the wall surface of the tubular element is cut by a cut 70 in the form of an inverse letter C. In other words, the cut 70 is cut in the tubular element in the form of an incomplete circle. The circle of the cut 70 is not cut through on the distal side, as can be seen from FIG. 11. The distal side of the cut 70 which is not cut through forms a hinge 71 for a tab 72. The tab 72 has a lower ear 73, an upper ear 74 and a tab centerpiece 75. The lower ear 73 abuts against an upper side of the tab centerpiece 75. The upper ear 74 abuts against a lower side of the tab centerpiece 75.

The tab 72 is manufactured as follows. The location of the cut 70 is set. In the middle of the cut 70, a hole 77 is cut. The cut 70 is formed by laser as shown in FIG. 2. The tab centerpiece 75 is supported from the rear, i.e., from the inside of the tubular element by a punch. The lower ear 73 is bent inwardly by 90 degrees relative to the tab centerpiece 75. The bending line of the ear 73 relative to the tab centerpiece 75 extends in parallel to the axis of the tubular element (in FIGS. 2 and 4 in the direction pointing to the left and the right). The upper ear 74 is equally bent inwardly by 90 degrees relative to the tab centerpiece 75. The bending line of the ear 74 relative to the tab centerpiece 75 also extends in parallel to the axis of the tubular element. After that, the tab centerpiece 75 is bent inwardly by 90 degrees. The bending line of the tab centerpiece 75 relative to the tubular element extends in the vertical cutting plane to the axis of the tubular element (in FIGS. 2 and 11 in the direction pointing upward and downward). In other words, the tab centerpiece 75 is bent inwardly by 90 degrees at the hinge 71. The tab centerpiece 75 is bent inwardly especially until a distal lateral edge of the lower ear 73 and a distal lateral edge of the upper ear 74 abut against the inner periphery of the tubular element (see FIG. 12).

The tab 72 serves as a support for a guide spring 8. In particular, the proximal surface of the tab centerpiece 75 forms a stop surface for the distal end of the guide spring 8. The two ears 73, 74 support the tab centerpiece 75 and absorb compressive forces acting from the guide spring 8 and forward them to the inner peripheral surface of the tubular element.

The tab centerpiece 75 has the centric hole 77. The hole 77 has a larger diameter than a control wire and a smaller diameter than the guide spring 8. The control wire is guided in the flexible portion 20 within the guide spring 8 and passes through the hole 70 and extends further into the deflecting portion A.

In the region K, tabs 72 are provided in the number of the control wires used (in the present embodiment: four). The tabs 72 are evenly spread in the peripheral direction of the tubular element.

Deflecting Portion A

The precise structure of the deflecting portion A is illustrated in FIGS. 13 to 18.

The deflecting portion A includes individual joint members 6 arranged in the longitudinal direction of the deflecting portion A. The individual joint members 6 are pivoting relative to each other. In FIGS. 13 and 14, three successively arranged joint members 6 are shown: a joint 61, a joint 62 proximally from the joint 61 and a joint 63 proximally from the joint 62.

The joint members 6 are equally designed except for the most distally located joint member 6 and the most proximally located joint member 6.

The structure of the respective joint member 6 will be discussed below by way of the joint member 62.

The joint member 62 is formed as a tubular portion of said tubular element by laser-cutting. The joint member 62 has distal boundary lines 601, 602, 603, 604 and 605 and proximal boundary lines 606, 607, 608 and 609 at the periphery of the tubular element.

The individual distal boundary lines are composed of one circularly shaped head line 601, two neck lines 602, two shoulder lines 603, two arm lines 604 and one arm end line 605. More exactly speaking, the distal side of the joint member 62 is formed as follows. The circularly shaped head line 601 forms an incomplete circle which merges at the proximal side on each side into a neck line 602. A shoulder line 603 which extends approximately perpendicularly to the axis of the tubular element is connected to each of the two neck lines 602. An arm line 604 which extends approximately in parallel to the axis of the tubular element in the distal direction is connected to each of the two shoulder lines 603. The two distal ends of the arm lines 604 are connected by an arm end line 605 which again extends perpendicularly to the axis of the tubular element.

Hence the joint member 62 includes a main body 621 from which each of a first head 622, a first arm 623, a second head 622 and a second arm 623 protrudes to the distal side about 90 degrees along an imaginary peripheral line extending perpendicularly to the axis of the joint member 62. Thus, the heads 622, 622 extend in a first imaginary plane. The arms 623, 623 extend in a second imaginary plane that is offset by 90 degrees against the first imaginary plane. The two heads 622, 622 of the joint member 62 form a pivot axis for the joint member 62 located distally therefrom.

Each head 622 is formed on the distal side by a head line 601. A constriction is formed by the neck lines 602 between the head 622 and the main body 621. The respective head 622 protrudes further in the distal direction than the respective arm 623.

The individual proximal boundary lines are composed of one curved foot line 606, two bottom lines 607, two straight foot lines 608 and one waist line 609. More precisely, the proximal side of the joint member 62 is formed as follows. The curved foot line 606 forms an incomplete circle that is open on the proximal side. At the open ends of the incomplete circle, the curved foot line 606 merges into each of the bottom lines 607 extending approximately perpendicularly to the axis of the tubular element.

A straight foot line 608 which extends approximately in parallel to the axis of the tubular element in the distal direction is connected to each of the two bottom lines 607. The two distal ends of the straight foot lines 608 are connected by a waist line 609 which in turn extends perpendicularly to the axis of the tubular element.

In this way, on the proximal side of the main body 621 the joint member 62 includes two feet 624 extending in the proximal direction. Each of the feet 624 has, in the direction of extension, a straight side at the straight foot line 608 and a curved side at the curved foot line 606.

In the region between the two straight foot lines 608, an arm of the proximally located joint member 63 is arranged to be movable in the longitudinal direction. In the region between the two curved foot lines 606, a head of the proximally located joint member 63 is fixedly held in the longitudinal direction. Only a slight movement due to play between the inner periphery of the curved foot line and the outer periphery of the circularly shaped head line is possible.

In the non-curved state of the deflecting portion A, the waist line 609 is spaced apart from the arm end line 605 of the proximally located joint member 63, as shown in FIG. 14. The arm end line 605 and the waist line 609 of the proximally located joint member 63 are parallel to each other.

In the non-curved state of the deflecting portion A, the bottom line 607 is spaced apart from the shoulder line 603 of the proximally located joint member 63, as shown in FIG. 14. The bottom line 607 and the shoulder line 603 of the proximally located joint member 63 may be in parallel to each other or approximately in parallel to each other or else slightly angled relative to each other, as shown in FIG. 14. Between the bottom line 607 and the shoulder line 603 of the proximally located joint member 63, not only a simple cut line has been produced, but the material of the tubular element has been cut out as a quadrangular piece.

A respective head 622 forms a coupling portion that is coupled to an adjacent joint member 6. The feet 624 constitute a guide portion engaged in an adjacent joint member 6 such that an axial movement of the joint members 6 relative to each other is possible.

Figure 17:
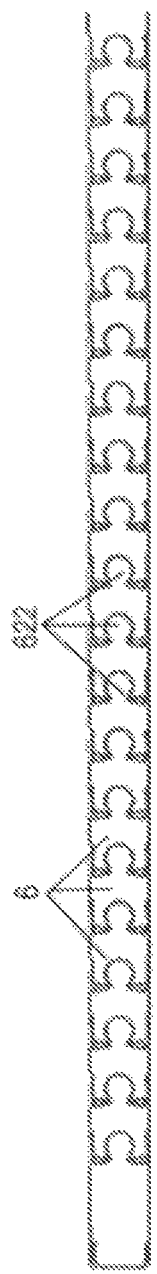
FIG. 17 shows a fragmentary schematic side view of the deflecting portion of the insertion tube according to the invention.

FIG. 17 illustrates a top view onto the deflecting portion A comprising the respective joint members 6. In the top view, the heads 622 of the joint members 6 are visible.

Figure 18:
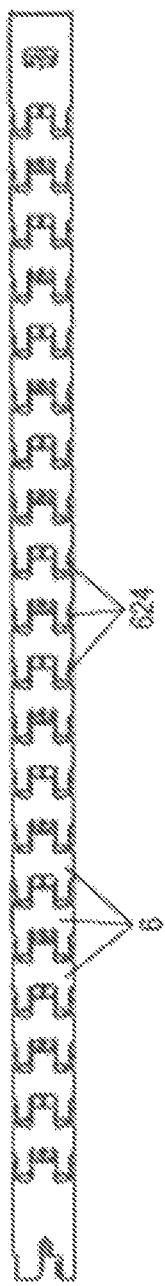
FIG. 18 shows a fragmentary schematic top view of the deflecting portion of FIG. 17.

FIG. 18 illustrates a side view of the deflecting portion A comprising the respective joint members 6. In the side view, the feet 624 of the joint members 6 are visible.

The most distally located joint member 6 includes no head and is shown in the FIGS. 2 and 17 to 21.

The most proximally located joint member 6 includes no foot and is shown in the FIGS. 2, 11 and 18.

In the embodiment, the deflecting portion A can be deflected in two deflecting directions, i.e., upward and downward in the FIGS. 13 and 14 (and FIG. 17), wherein the respective heads 622 of the joint members 6 form bending axes of the joint members 6. In other words, the deflecting portion A in FIG. 17 is upwardly and downwardly pivotable. In the representation of FIG. 18, the deflecting portion A is pivotable toward the viewer and away from the viewer.

Figure 15:
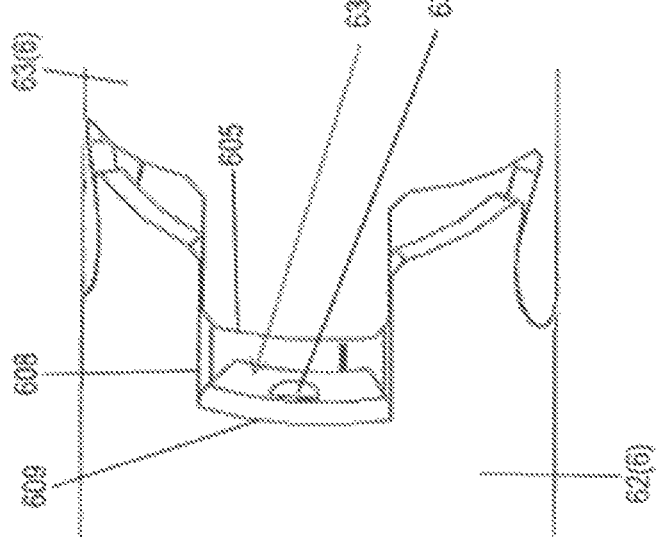
FIG. 15 shows a fragmentary schematic view of part of the deflecting portion of the insertion tube according to the invention, with a cable guide being shown.
Figure 16:
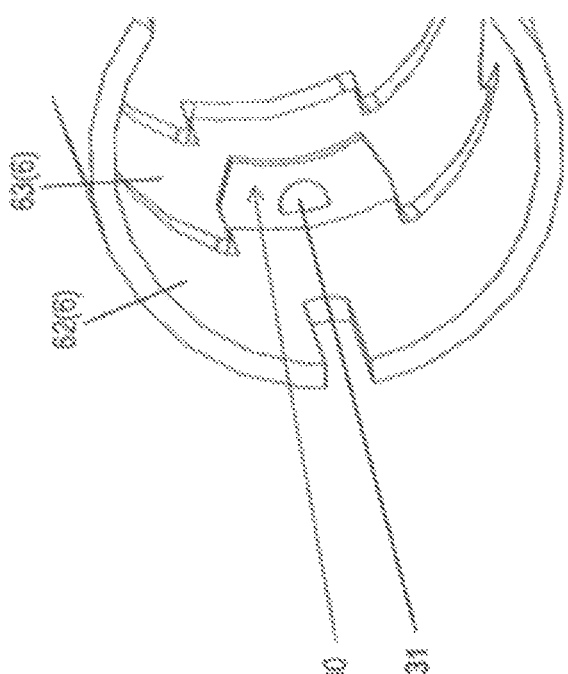
FIG. 16 shows a fragmentary perspective view of the cable guide from FIG. 14.

As illustrated in FIGS. 15 and 16, the waist line 609 forms a hinge portion for a cable guide tab 630. The cable guide tab 630 extends from the waist line 609. A material portion extending along the straight foot lines 608 to the arm end line 605 of the proximally located joint member 63 is used for the cable guide tab 630. The cable guide tab 630 is articulated to the waist line 609 and is curved inwardly about 90 degrees. The cable guide tab 630 includes a centric hole 631. The hole 631 has a larger diameter than the control wire.

Each of the joint members 6 includes the cable guide tabs 630 including the hole 631 such that the cable guide tabs 630 for a specific control wire are arranged successively in the longitudinal direction of the deflecting portion A. The cable guide tabs 630 serve as guide projections on which a control wire is supported. Thus, the cable guide tabs 630 guide the associated control wire through the deflecting portion A.

The joint members 6 may be arranged on the deflecting portion A so that their heads face the proximal direction, as shown in FIG. 17. Alternatively, the joint members 6 may be arranged on the deflecting portion A so that their heads face the distal direction, as indicated in FIG. 13.

The distal end of the deflecting portion A is shown in FIGS. 19 to 21. In FIGS. 19 to 21, the most distally located joint member 69 of the deflecting portion A is visible. In this most distally located joint member 69, the distal side of the control wire 9 is anchored. The control wire 9 extends from the control body 3 to the most distally located joint member 69 of the deflecting portion A.

Fastening of the Control Wire

The precise fastening of the control wire 9 is illustrated in FIGS. 22 and 23.

The control wire 9 is fastened to the control wheel G in the control body 3. When the control wheel G is rotated in a tensioning direction, the control wire 9 is tensioned. When the control wheel G is rotated in the relieving direction opposite to the tensioning direction, the control wire 9 is relieved.

The control wire 9 extends from the control body 3 extending in the insertion tube 2 toward the joint member 69 and forms a first portion 91. Said first portion 91 of the control wire 9 extends along the inner periphery of the insertion tube 2. Said first portion 91 of the control wire 9 is shown by way of the reference numeral 91 in FIG. 22. On the distal side of the joint member 69, a slit 691 penetrating the peripheral wall of the joint member 69 is configured (see FIG. 20) which slit extends in the longitudinal direction of the joint member 69. Another similar slit 692 is provided on the distal side of the joint member 69 and is diametrically opposed to the slit 691.

The control wire 9 extends along the inner periphery of the joint member 69 in the distal direction and penetrates the slit 691 to the outside, is wound at the outer periphery of the joint member 69 in the peripheral direction of the joint member 69 to the slit 692, penetrates the slit 692 to the inside and extends along the inner periphery of the joint member 69 in the proximal direction to the control wheel G in the control body 3.

Consequently, the control wire 9 is divided into a first portion 91 extending from the control wheel G within the control body 3 to the slit 691, a second portion 92 extending from the slit 691 at the outer periphery of the joint member 69 in the peripheral direction of the joint member 69 to the slit 692, and a third portion 93 extending from the slit 692 to the control wheel G in the control body 3.

By rotation of the control wheel G in the tensioning direction, the control wire 9 is tensioned and thus the deflecting portion A is deflected, as the third portion 93 anchored on the joint member 69 is urged in the proximal direction. The third portion 93 of the control wire 9 thus constitutes a distal anchoring portion of the control wire 9.

Manufacturing Method

The insertion tube 2 according to the invention can be manufactured by one single tubular element which is cut by laser. The tubular element is made from a relatively hard material such as, e.g., stainless steel or else suitably hard plastic material. The initially hard tubular element is made flexible by the cuts, although it retains its rigidity.

The cuts produce the respective lateral incisions (cuts extending perpendicularly to the axis) 98, 99 in the proximal passive flexible portion 20, the hole 77, the cut 70 in the transition region K, the hole 631, the respective joint members 6 in the distal deflecting portion A and the slits 691, 692. This order is not meant to be a limitation. For example, the slits 691, 692 may be cut before the joint members 6. Moreover, the order of the cuts may also be reversed.

The flexibility as well as the rigidity of the tubular element can be controlled by way of the shape, the arrangement and the size of the cuts.

The location of the respective cuts can be calculated in advance and predetermined. In a programmable laser cutter, the predefined data for the respective cuts can be entered to automatically produce the insertion tube 2.

The individual joint members 6 are completely cut out and form bodies physically separated from each other which are merely connected by form fit.

After laser-cutting of the tubular element, the tabs 72 and the cable guide tabs 630 are inwardly bent. Thus, the blank for the insertion tube 2 is finished.

Now the control wire 9 can be inserted and fastened in said blank for the insertion tube 2. The blank for the insertion tube 2 can be fastened to the control body 3. Further, a coating surrounding the blank for the insertion tube 2 and preferably being made from metal for shielding the electric control and onto said coating an elastic jacket made from plastic or rubber can be mounted onto the blank for the insertion tube 2. The elastic jacket of plastic or rubber can be subjected to thermal shrinking.

SECOND EMBODIMENT

Hereinafter, a second embodiment of the present invention will be described with reference to FIG. 24.

FIG. 24 illustrates a fragmentary schematic representation of the proximal passive flexible portion that is applied in the second embodiment.

The proximal passive flexible portion 20 structured according to the principle shown in FIG. 24 can replace the proximal passive flexible portion 20 of the first embodiment. In other words, the control body 3 and the deflecting portion A can be combined with the proximal passive flexible portion 20 of the present second embodiment.

As afore-described, the distal deflecting portion A and the proximal passive flexible portion 20 having the three zones B, C and D are formed of one single tube or hose, see also FIG. 1.

Zone B constitutes a transition region B between the central region C and the deflecting portion A. Zone C constitutes the central region C. Zone D constitutes a connecting region D of the proximal passive flexible portion 20 at the control body 3. In other words, the entire insertion tube including the connecting region D at the control body 3, the central region C, the transition region B between the central region C and the deflecting portion A, and the deflecting portion A is manufactured from one single tubular element.

For clarity, FIG. 1 shows the proximal passive flexible portion 20 as if the three zones B, C and D were equal in length relative to each other along the longitudinal direction of the insertion tube 2, which is not the case, of course. The central region C is longer than the transition region B and the connecting region D. The central region C is longest in the proximal passive flexible portion 20. In other words, the actual proximal passive flexible portion 20 is formed by the structure of the central region C. The bending characteristics, the elasticity and the torsional resistance of the proximal passive flexible portion 20 are materialized by the structure of the central region C.

Hereinafter, the structure of the central region C of the proximal passive flexible portion 20 will be described in detail by way of FIG. 24.

The proximal passive flexible portion 20 is manufactured from the already afore-described tubular element. In the central region C, a plurality of main cuts 990 are cut along the longitudinal direction of the tubular element by laser-cutting. These main cuts 990 extend in parallel to each other. The main cuts 990 extend perpendicularly to the axis of the tubular element.

More precisely, the main cuts 990 extend along the periphery of the central region C in an interrupted manner so that non-cut stays 992 are left between main cut portions located on a peripheral line. In the present embodiment, four main cut portions are configured, when viewed in the peripheral direction.

FIG. 24 illustrates said main cut portions more precisely. FIG. 24 shows a first sequence of main cut portions formed in the peripheral direction denoted with the reference numerals 990A, 990B and 990C. Moreover, FIG. 24 shows a second sequence of main cut portions formed in the peripheral direction denoted with the reference numerals 990A1 and 990B1. The first sequence of main cut portions with the reference numerals 990A, 990B and 990C is adjacent in the longitudinal direction to the second sequence of main cut portions formed in the peripheral direction with the reference numerals 990A1 and 990B1. The length of the main cut portions in the peripheral direction is always the same. That is, not only is the length of the main cut portions in the peripheral direction of a particular sequence of main cut portions equal to each other, but the length of the main cut portions in the peripheral direction of all sequences of main cut portions in the entire central region C is equal to each other.

In the first sequence of main cut portions shown in FIG. 24 a first main cut portion 990A, a second main cut portion 990B and a third main cut portion 990C are shown. A fourth main cut portion that is not visible is located on the side of the tubular element remote from the viewer behind the plane of projection. The first main cut portion 990A, the second main cut portion 990B, the third main cut portion 990C and the fourth main cut portion that is not shown are configured successively in the peripheral direction of the tubular element. Thus, the tubular element is cut at said peripheral line four times in portions of equal length. A respective stay 992 is left between an end of the first main cut portion 990A and a beginning of the second main cut portion 990B, an end of the second main cut portion 990B and a beginning of the third main cut portion 990C, an end of the third main cut portion 990C and a beginning of the fourth main cut portion (not shown), and an end of the fourth main cut portion (not shown) and a beginning of the first main cut portion 990A. The tubular element is not cut at this region of the stay 992.

In the second sequence of main cut portions shown in FIG. 24, a first main cut portion 990A1 and a second main cut portion 990B1 are shown. A third main cut portion (not visible) and a fourth main cut portion (not visible) are located on the side of the tubular element remote from the viewer behind the plane of projection.

The main cut portions of the second sequence are arranged to be offset relative to the main cut portions of the first sequence. The region of the first sequence, where the main cut portions 990A, 990B and 990C leave the respective stay 992, in the adjacent second sequence corresponds to a region that forms the center of the main cut portion 990A1 and 990B1, when viewed in the peripheral direction of the tubular element. The stays are thus positioned to be offset by 45 degrees from sequence to sequence of the main cuts 990 in the longitudinal direction of the tubular element.

The cutting width of all main cuts 990 in the tubular element is equal. The distance of all sequences of the main cuts 990 in the tubular element is equal to each other.

In the longitudinal direction of the tubular element, a respective secondary cut 991 is provided adjacent to each stay 992, as shown in FIG. 24.

On both sides in the longitudinal direction of the tubular element, a secondary cut 991 is configured adjacent to the stay 992. The secondary cut 991 is shorter than the main cut 990. The secondary cut 991 overlaps the ends of the adjacent main cuts 990.

All of the secondary cuts 991 have the same length relative to each other in the peripheral direction of the tubular element. All of the secondary cuts 991 are in parallel to each other as well as in parallel to the main cuts 990.

Each sequence of secondary cuts 991 is associated with a sequence of main cuts 990 adjacent to both sides in the longitudinal direction of the tubular element. In other words, each sequence of main cuts 990 has a proximal sequence of secondary cuts 991 and a distal sequence of secondary cuts 991.

Consequently, when viewed along the longitudinal direction of the tubular element, a sequence of main cuts 990 is followed by a distal sequence of secondary cuts 991 which in turn is followed by a proximal sequence of secondary cuts 991 of the next sequence of main cuts 990. When viewed along the longitudinal direction of the tubular element, a sequence of secondary cuts 991 on one side has a neighboring further sequence of secondary cuts 991 and on the other side has a neighboring sequence of main cuts 990.

The secondary cuts 991 are configured in the longitudinal direction of the tubular element closer to the next main cuts 990 than to the next secondary cuts 991.

In other words, adjacent to the main cuts 990, secondary cuts 991 are provided such that they are arranged to be closer to the adjacent main cuts 990 than to the adjacent secondary cuts 991.

For the purpose of illustration, FIG. 24 shows the secondary cuts 991 for the first sequence of main cut portions as secondary cuts 991a and the secondary cuts 991 for the second sequence of main cut portions as secondary cuts 991b. The secondary cuts 991a for the first sequence of main cut portions are arranged to be closer to the adjacent main cut portions 990A, 990B and 990C than to the adjacent secondary cuts 991b. Thus, adjacent cuts in the tubular element do not have the same distance.

The cutting width of all secondary cuts 991 in the tubular element is equal. The cutting width of the secondary cuts 991 is narrower than the cutting width of the main cuts 990.

Effect of the Second Embodiment

As in the first embodiment, the structure of the second embodiment ensures an insertion tube 2 with very high flexibility and, at the same time, high torsional resistance.

Further Alternatives

In the first and second embodiments, the flexible portion 20 includes, when viewed in the proximal direction, a first zone B, a second zone C and a third zone D of different flexibility. The number of zones or regions of different flexibility is not limited. The flexible portion 20 may also include more or fewer zones of different flexibility. The invention is also applicable to an insertion tube in which the flexible portion 20 has a continuously constant flexibility.

In the first and second embodiments, the tubular element of the insertion tube 2 is made from stainless steel. The invention is not limited thereto. The material of the insertion tube 2 may be any sufficiently rigid material such as rigid plastic material. In another alternative, Nitinol (a nickel-titanium alloy) can be used as tube material. This material has, inter alia, the characteristic of a so-called super-elasticity, i.e., it can be elastically deformed in large areas without being permanently bent.

In the first and second embodiments, cuts are provided in the tubular element by a laser cutter. Said cuts may be very precisely provided. Therefore, manufacture by laser is preferred. Basically, it is imaginable, however, that said cuts are also produced by other manufacturing processes such as sawing, wire sawing, etc.

In the first and second embodiments, the deflecting portion A can be deflected into two deflecting directions, viz. upward and downward in FIGS. 6 and 7. In an alternative, the individual joint members 6 may be configured such that their heads 622 are offset from joint member 6 to joint member 6, being rotated about 90 degrees about the axis of the deflecting portion A (axis of the joint members 6). In this alternative, the deflecting portion A can be deflected into four deflecting directions, viz. upward and downward in FIGS. 6 and 7 as well as toward the viewer and away from the viewer.

In the alternative in which the deflecting portion A can be deflected into four deflecting directions, two control wires 9 can be used which extend inside the insertion tube 2 being offset by 90 degrees against each other. The joint member 92 then is provided with four distal slits which are equally offset by 90 degrees against each other.

In the embodiment, a respective joint member 6 is configured in the described form. The invention is not limited to the form of the joint member 6. It is sufficient when joint members which are coupled to each other and allow for a deflecting movement of the deflecting portion A are cut in the deflecting portion A.

The proximal passive flexible portion C structured according to the principle shown in FIG. 24 can be applied to the first or second embodiment. This means that the proximal passive flexible portion C shown in FIG. 24 forms part of the integral tubular element for the entire insertion tube 20. The tubular element for the entire insertion tube 20 including the proximal passive flexible portion C is thus manufactured from a tubular element by laser-cutting.

As an alternative, in the first or second embodiment the proximal passive flexible portion C can be manufactured separately from the remaining insertion tube 20.

In the embodiment of FIG. 24, in the longitudinal direction of the tubular element two respective secondary cuts are disposed adjacent to the stay on both sides of the stay. In one alternative, in the longitudinal direction of the tubular element a respective secondary cut may be arranged adjacent to the stay on one side of the stay.

In the first embodiment, the main cuts are provided so that, along the periphery of the tubular element, two stays remain between the main cut portions.

In the second embodiment, the main cuts are provided so that, along the periphery of the tubular element, four stays remain between the main cut portions.

The invention is not limited thereto. Preferably, the number of stays along the periphery of the tubular element between the main cut portions is at least two or more and may be any number.

In the first embodiment, the cutting width of the main cuts 98 is larger than the cutting width of the secondary cuts 99. In the second embodiment, too, the cutting width of the main cuts may be larger than the cutting width of the secondary cuts. The principle of the invention is also applicable to a case, however, in which the cutting width of the main cuts is equal to the cutting width of the secondary cuts.

The invention can be advantageously applied to a duodenoscope, a gastroscope, a colonoscope or similar endoscope. The principle of the invention can also be applied to any other type of endoscope.

The principle of the invention is also applicable to other medical devices which make use of an insertion tube.

LIST OF REFERENCE NUMERALS

1 endoscope
2 insertion tube, pipe
3 control body
6 joint member
8 guide spring
9 control wire
20 flexible portion
61 joint member
62 joint member
63 joint member
69 most distally located joint member
70 cut
71 hinge
72 tab
73 lower ear
74 upper ear
75 tab centerpiece
77 hole
91 first portion of control wire
92 second portion of control wire
93 third portion of control wire
97 stay
98 main cut
99 secondary cut
201 cut from the top
202 cut from the bottom
203 non-cut clearance
204 cut from the side
601 head line
602 neck line
603 shoulder line
604 arm line
605 arm end line
606 curved foot line
607 bottom line
608 straight foot line
609 waist line
621 main body
622 head
623 arm
624 foot
630 cable guide tab
631 centric hole
691 slit
692 slit
801 cut from the top
802 cut from the bottom
803 non-cut clearance
805 annular portion including short cuts
811 short cut from the top
812 short cut from the bottom
880 cable guide tab
990 main cut
991 secondary cut
992 stay
1000 insertion tube 1001 metal leaf spiral
1002 metal leaf spiral
1003 metal mesh
1004 plastic coating
A deflecting portion
A' deflecting portion
B first zone (distal region)
C second zone (central region)
D third zone (proximal region)
F first control wheel (first control element)
G second control wheel (second control element)
H distance
J control body housing
K transition region
L longitudinal line of the tube 2
M distance
N distance
X region responsible for the creation of high flexibility of the tube 2
Y region responsible for the creation of high torsional resistance of the tube 2

The invention claimed is:

1. A method for manufacturing an insertion tube of an endoscope from a tubular element, wherein the insertion tube includes a proximal passive flexible portion, a distal deflecting portion, and a transition region between the proximal passive flexible portion and distal deflecting portion, the method comprising:
providing, in the proximal passive flexible portion, cuts to enable the proximal passive flexible portion to be bent, wherein the cuts are provided in the proximal passive flexible portion so that a distance between adjacent cuts is not the same;
cutting a distally-facing C-shaped cutout portion in wall surface in the insertion tube at the transition region; and
bending the cutout portion to form a tab having a center portion and inwardly extending perpendicular to a longitudinal axis of the insertion tube to form:
an upper ear portion perpendicular to and distally extending from a center portion of the tab, and
a lower ear portion distally extending from a center portion of the tab and facing the upper ear portion, with the center portion of the tab between the upper and lower ear portion.

2. The method according to claim 1, further comprising:
providing, in the proximal passive flexible portion, main cuts which have the same distance from each other in the longitudinal direction of the proximal passive flexible portion, and
providing, adjacent to the main cuts, in the proximal passive flexible portion secondary cuts which are arranged, in the longitudinal direction of the proximal passive flexible portion, to be closer to the adjacent main cuts on one side of the secondary cuts than to the adjacent main cuts on the other side of the secondary cuts.

3. The method according to claim 2, wherein
the main cuts are cut in parallel to each other.

4. The method according to claim 2, wherein
the main cuts are cut in an interrupted manner along the periphery of the proximal passive flexible portion such that non-cut stays are left between main cut portions located on a peripheral line.

5. The method according to claim 4, wherein
each of the secondary cuts is cut adjacent to a stay between main cut portions located on a peripheral line.

6. The method according to claim 5, wherein
one secondary cut is respectively cut in the longitudinal direction of the proximal passive flexible portion adjacent to the stay on one side of the stay.

7. The method according to claim 5, wherein
two secondary cuts are respectively cut in the longitudinal direction of the proximal passive flexible portion adjacent to the stay on both sides of the stay.

8. The method according to claim 2, wherein
the main cuts are cut to be wider than the secondary cuts.

9. The method according to claim 1,
further comprising manufacturing from one single tubular element, an entirety of the insertion tube including a connecting region of the proximal passive flexible portion at a control body, the proximal passive flexible portion, the transition region between the proximal passive flexible portion and the deflecting portion, and the deflecting portion.

10. The method according to claim 1, further comprising cutting by laser an entirety of the cuts of the insertion tube.

11. An endoscope comprising:
an insertion tube comprising:
a proximal passive flexible portion, a distal deflecting portion, and a transition region between the proximal passive flexible portion and distal deflecting portion;
cuts in the proximal passive flexible portion configured such that the proximal passive flexible portion is bendable, wherein a distance between adjacent cuts in the proximal passive flexible portion is not the same;
a tab inwardly extending perpendicular to a longitudinal axis of the insertion tube and having a center plate;
an upper ear portion perpendicular to and distally extending from the center plate of the tab, and
a lower ear portion distally extending from the center plate of the tab and facing the upper ear portion, with the center plate of the tab between the upper and lower ear portion.

12. The endoscope according to claim 11, wherein
the proximal passive flexible portion includes main cuts which have the same distance from each other in the longitudinal direction of the proximal passive flexible portion, and,
adjacent to the main cuts, the proximal passive flexible portion includes secondary cuts which, in the longitudinal direction of the proximal passive flexible portion, are arranged to be closer to the adjacent main cuts on one side of the secondary cuts than to the adjacent main cuts on the other side of the secondary cuts.

13. The endoscope according to claim 12, wherein
the main cuts are in parallel to each other.

14. The endoscope according to claim 12, wherein
the main cuts extend in an interrupted manner along the periphery of the proximal passive flexible portion such that non-cut stays are left between main cut portions located on a peripheral line.

15. The endoscope according to claim 14, wherein
each of the secondary cuts is arranged adjacent to a stay between main cut portions located on a peripheral line.

16. The endoscope according to claim 15, wherein
one secondary cut is respectively arranged in the longitudinal direction of the proximal passive flexible portion adjacent to the stay on one side of the stay.

17. The endoscope according to claim 15, wherein
two secondary cuts are respectively arranged in the longitudinal direction of the proximal passive flexible portion adjacent to the stay on both sides of the stay.
18. The endoscope according to claim 12, wherein
the main cuts are wider than the secondary cuts.
19. The endoscope according to claim 11, wherein
an entirety of the insertion tube includes a connecting region of the proximal passive flexible portion at a control body, the proximal passive flexible portion, the transition region between the proximal passive flexible portion and the deflecting portion, and the deflecting portion is manufactured from one single tubular element.
20. The endoscope according to claim 11, wherein
an entirety of the cuts in the insertion tube are made by laser.

* * * * *